United States Patent
Onodera et al.

(10) Patent No.: US 6,602,812 B1
(45) Date of Patent: Aug. 5, 2003

(54) PROCESS FOR PRODUCING LEUKOCYTE-REMOVING MATERIAL AND HYDROPHILIZED POLYOLEFINS

(75) Inventors: Hirokazu Onodera, Oita (JP); Makoto Yoshida, Oita (JP)

(73) Assignee: Asahi Medical Co., Ltd., Tokyo (JP)

( * ) Notice: Subject to any disclaimer, the term of this patent is extended or adjusted under 35 U.S.C. 154(b) by 0 days.

(21) Appl. No.: 09/486,064

(22) PCT Filed: Aug. 21, 1998

(86) PCT No.: PCT/JP98/03706

§ 371 (c)(1),
(2), (4) Date: Feb. 22, 2000

(87) PCT Pub. No.: WO99/10025

PCT Pub. Date: Mar. 4, 1999

(30) Foreign Application Priority Data

Aug. 22, 1997 (JP) ................................................ 9-240281

(51) Int. Cl.⁷ ................................................ B01D 39/00
(52) U.S. Cl. ..................... 442/327; 210/500.1; 442/327
(58) Field of Search ................................. 210/94, 500.1; 442/327

(56) References Cited

U.S. PATENT DOCUMENTS 5,186,835 A  *  2/1993  Masuoka et al. ...... 210/500.36

FOREIGN PATENT DOCUMENTS

| EP | 0329303 A1 | 8/1989 |
|----|------------|--------|
| JP | 54-18476 | 2/1979 |
| JP | 61-120602 | 6/1986 |
| JP | 62-7401 | 1/1987 |
| JP | 1-256971 | 10/1989 |
| JP | 2-21917 | 1/1990 |
| JP | 3-27317 | 2/1991 |

* cited by examiner

*Primary Examiner*—Terrel Morris
*Assistant Examiner*—Alexis Wachtel
(74) *Attorney, Agent, or Firm*—Young & Thompson

(57) ABSTRACT

A leukocyte-removing material composed substantially of a polyolefin, the factor of hydrophilicity of the surface of said leukocyte-removing material being less than 40% and not less than 30%.

31 Claims, No Drawings

PROCESS FOR PRODUCING LEUKOCYTE-REMOVING MATERIAL AND HYDROPHILIZED POLYOLEFINS

TECHNICAL FIELD

This invention relates to a leukocyte-removing material composed mainly of a hydrophobic polyolefin and a process for producing a hydrophilized polyolefin material suitable as said leukocyte-removing-material.

BACKGROUND ART

In recent years, various adverse side effects due to contamination with leukocytes have been known in the field of blood transfusion. For preventing the side effects, leukocytes are removed by using a material such as highly hydrophilic polyester nonwoven fabric or cotton fabric. In the transfusion of a platelet product, a technique of coating the surface of a leukocyte-removing material with a hydrophilic polymer or the like is employed for suppressing the adhesion of platelets to the leukocyte-removing material.

On the other hand, improvements have been made in techniques for selectively removing leukocytes for curing autoimmune diseases such as systemic lupus erythematosus, malignant rheumatoid arthritis, multiple sclerosis, ulcerative colitis and Crohn disease, leukemia, cancer, etc., or for immunosuppression before transplantation.

Materials such as highly hydrophilic polyester nonwoven fabric, cotton fabric, etc. have been widely used as leukocyte-removing materials because of their high leukocyte-removing capability. From the viewpoint of compatibility at the time of contact with blood, an ester structure or an amide structure is generally given to a leukocyte-removing material in order to impart hydrophilicity to the blood contact surface of the material. Such leukocyte-removing materials, however, are thermally unstable in the excess of attachment of importance to hydrophilicity. Particularly when the materials are subjected to wet heat sterilization or the like, their hydrolysis or the like is liable to take place. Thus, they are not always satisfactory as materials for medical supplies.

JP-A-3-27317 discloses a leukocyte-removing material obtained by grafting a monomer onto polyester fiber having a pore major axis of 0.5 to 4 μm and a CWST (critical wet surface tension) of 55 to 80 dyne/cm, by means of a radiation. This material, however, is poor in thermal strength because the polyester fiber or the aforesaid monomer has ester linkages. Therefore, the grafted monomer is liable to be released by dissolution during wet heat sterilization.

On the other hand, polyolefins are materials having an excellent thermal stability and they can be said to be preferable as materials for medical supplies which should be sterilized by high energy, such as wet heat sterilization, because they retain their strength as the materials even after the sterilization. The polyolefins, however, have a CWST of approximately 25 dyne/cm–30 dyne/cm and hence it has been not suitable to utilize them as they are.

Therefore, JP-A-1-256971 discloses a leukocyte-removing material comprising polypropylene nonwoven fabric hydrophilized by plasma treatment. However, the plasma treatment can impart hydrophilicity to the material temporarily but the imparted hydrophilicity decreases with the lapse of time. Thus, the hydrophilicity cannot be stably retained for a long period of time. Such a leukocyte-removing material is used immediately after the hydrophilization in rare cases and hence should be kept hydrophilized for a certain period or permanently. Accordingly, the hydrophilization by the plasma treatment is not desirable. In addition, when the plasma treatment is carried out, a considerable amount of electric charge is produced for increasing the hydrophilicity, so that the possibility of complement activation and bradykinin production is increased. Thus, the material hydrophilized by the plasma treatment is not desirable as a material for treating blood.

In view of such problems, the present invention is intended to provide a leukocyte-removing material which is hardly decomposed even by wet heat sterilization and has a stable hydrophilicity, and to provide a material which can retain hydrophilicity permanently irrespective of the hydrophobicity of a raw material therefor, has good priming properties, and has an excellent ability to remove leukocytes selectively.

Furthermore, the present invention is intended to provide a process for producing a hydrophilized polyolefin which retains its hydrophilicity for a long period of time, without greatly changing characteristics of polyolefin.

DISCLOSURE OF THE INVENTION

The present inventors eanestly investigated in order to solve the problems described above, and consequently found that a leukocyte-removing material comprising a polyolefin and having a factor of hydrophilicity of less than 40% and not less than 30% is very effective. Moreover, the present inventors found that the above-mentioned leukocyte-removing material possesses greatly improved priming properties and is surprisingly stable to wet heat sterilization, whereby the present invention has been accomplished.

Thus, one aspect of the present invention is directed to a leukocyte-removing material composed substantially of a polyolefin and having a factor of hydrophilicity of less than 40% and not less than 30%.

Another aspect of the present invention is directed to a process for producing a hydrophilized polyolefin which comprises a step of irradiating substantially a polyolefin with a radiation in a dose of less than 300 kGy and not less than 15 kGy, and a step of heating said polyolefin at a temperature of lower than 125° C. and not lower than 75° C. after the irradiation with the radiation.

The term "leukocyte-removing material" used herein means a material for removing leukocytes from a leukocyte-containing fluid such as blood or a body fluid by a mechanism such as filtration or adsorption.

BEST MODE FOR CARRYING OUT THE INVENTION

In the leukocyte-removing material of the present invention, the term "composed substantially of a polyolefin" means that the leukocyte-removing material is composed essentially of a modified polyolefin obtained by imparting hydrophilicity to naturally hydrophobic polyolefin by modification. In detail, the term means that the leukocyte-removing material is composed of a product obtained by changing (modifying) a polyolefin itself, for example, by irradiation with a radiation without converting the polyolefin to another material.

Therefore, the leukocyte-removing material "composed substantially of a polyolefin" of the present invention does not include, for example, products obtained by grafting a hydrophilic monomer as another component onto a polyolefin, and products obtained by coating a polyolefin with a hydrophilic monomer as another component.

The leukocyte-removing material of the present invention may contain antioxidants and stabilizers, which are usually contained in polyolefins. In addition, the leukocyte-removing material of the present invention may contain a small amount of a hydrophobic polymer other than the polyolefin, for holding of the polyolefin.

The polyolefin refers to a polymer obtained by homopolymerization or copolymerization of one or more alkenes or alkynes. The polyolefin includes, for example, polyolefins obtained by homopolymerization, such as polyethylenes, polypropylenes, polybutylenes, etc., and polyolefins obtained by copolymerization, such as polypropylene-polyethylene copolymers, polybutylene-polypropylene copolymers, etc. From the viewpoint of thermal strength, the polypropylenes, polybutylenes, polyethylene-polypropylene copolymers, polyethylene-polybutylene copolymers, etc. are preferable. From the viewpoint of the controllability of the leukocyte-removing material, the polypropylenes, polypropylene-polyethylene copolymers, etc. are the most preferable.

The term "factor of hydrophilicity" used herein is defined as follow: there are prepared aqueous ethanol solutions having predetermined and stepwise varied weight ratios of ethanol to water, a droplet (volume: about $10\mu L$) of each of the solutions is brought into contact with a leukocyte-removing material, starting from the lowest concentration, and a concentration of the aqueous ethanol solution at which said leukocyte-removing material is wetted for the first time is called the factor of hydrophilicity. However, depending on the material, the material is not completely wetted in some cases because the wetting is dependent on the density of the material. In this case, the factor of hydrophilicity referred to herein is defined as a concentration of the aqueous ethanol solution at which the contact angle becomes 120° or more. The term "contact angle" used here means an angle between the droplet and said leukocyte-removing material. When the contact angle is measured on the spherical surface or cylindrical surface of a fiber or the like, it is defined as an angle made by the droplet outer surface and a tangent between the material surface and the center of the droplet. That is, the contact angle is defined as an angle made by the droplet and a tangent to the material which touches the material surface at the center of the droplet on the portion on which the droplet is in contact with the material. The contact angle can be measured with a well-known contact angle measuring apparatus.

The factor of hydrophilicity of each fibrous material measured by this method is 43% for polyethylene nonwoven fabric, 41% for polypropylene nonwoven fabric and 43% for polybutylene fiber. All polyolefin fibers having a usual composition have a factor of hydrophilicity of more than 40%.

The leukocyte-removing material of the present invention should be weakly hydrophilic to such an extent that the factor of hydrophilicity is less than 40% and not less than 30%, from the viewpoint of priming properties, affinity for blood, and low stimulating properties for blood.

When the factor of hydrophilicity of the material is 40% or more, the material has a high hydrophobicity and a low affinity for plasma, so that it repels blood. Therefore, such a material is not suitable. In addition, when the factor of hydrophilicity of the material is 40% or more, the material cannot be primed with water unless it is pretreated with a solution having a relatively high affinity for the material, such as ethanol. Therefore, troublesome operations are required for priming. Thus, such a material is not suitable.

On the other hand, when the factor of hydrophilicity is less than 30%, the material is increased in hydrophilicity, so that its priming properties are improved. But, the presence of hydrophilic groups increases the possibility of the activation of a large amount of complements and the production of bradykinin during blood treatment. Therefore, such a material is also not suitable.

Polyolefin materials having such a hydrophilicity imparted by irradiation with a radiation that the factor of hydrophilicity is less than 30% possess a deteriorated strength and hence are not suitable as materials for medical supplies for removing leukocytes.

The factor of hydrophilicity is preferably less than 40% and not less than 31%, more preferably less than 39% and not less than 32%.

A porous leukocyte-removing material composed substantially of a polyolefin and having the factor of hydrophilicity according to the present invention can be obtained by a method of giving, for example, hydroxyl groups and/or keto groups to a material having a factor of hydrophilicity of 40% or more, to adjust the factor of hydrophilicity to less than 40% and not less than 30%. Specifically, the factor of hydrophilicity of the leukocyte-removing material can be adjusted to a value in a desirable range by giving hydroxyl groups and/or keto groups by any of ① a method of hydrolyzing ester groups or ether groups naturally present in the material, ② a method of irradiating a polyolefin with a radiation in the presence of oxygen to form a peroxide surface, and ③ a method of causing a chemical reaction by the use of an oxidizing agent such as sulfuric acid.

Of these, the method of irradiating a polyolefin having no hydroxyl group with a radiation in the presence of oxygen makes it possible to give hydroxyl groups and/or keto groups so as to attain a desirable factor of hydrophilicity, most satisfactorily and easily. When the irradiation with a radiation is carried out in air or in the presence of oxygen, a peroxide is produced in the material. Hydroxyl groups can be introduced onto the surface by cleaving radicals by pyrolizing this peroxide in the presence of water or subjecting the peroxide to redox decomposition with a reducing agent. Keto groups can also be efficiently introduced by the recombination of radicals which takes place simultaneously. As the radiation, electron beams are most preferably used from the viewpoint of, in particular, transmittance.

A leukocyte-removing material obtained by irradiating a polyolefin with a radiation in a dose of less than 300 kGy and not less than 15 kGy and heating the polyolefin at a temperature of lower than 125° C. and not lower than 75° C. after the irradiation is preferable from the viewpoint of, in particular, stability of hydrophilicity and biocompatibility.

When a slight amount of hydroxyl groups are given to a polyolefin, any of the well-known methods described above may be adopted, though it it preferable to give hydroxyl groups and/or keto groups by covalent binding.

The leukocyte-removing material of the present invention preferably has hydroxyl groups and/or keto groups on the material surface.

The word "surface" used herein means a face which can come in contact with blood, and it does not include the inside of the material and internal faces, with which blood cannot come in contact. Therefore, whatever values the factor of hydrophilicity of such portions (the inside of the material and internal surfaces) may have, they need not be taken into consideration in determining the factor of hydrophilicity of the surface of the leukocyte-removing material of the present invention.

The leukocyte-removing material of the present invention preferably comprises, in particular, at least a polypropylene-polypropylene alcohol. The polypropylene-polypropylene alcohol may be either a copolymer of propylene and propylene alcohol, or a material obtained by giving hydroxyl groups to a polypropylene subsequently by covalent binding.

In the leukocyte-removing material of the present invention, a porous material having through-holes is effectively used as a raw material. Preferable examples of form of the porous material are a fibrous form, spongy form, foam, etc. Of materials of these forms, fibrous materials are particularly satisfactorily used as the leukocyte-removing material from the viewpoint of production and the leukocyte-removing capability of the final product. Preferable specific examples of form of the fibrous materials are a fibrous form, cotton form, thread form, bundle form, reed screen form, woven fabric form and nonwoven fabric form. Woven fabric and nonwoven fabric are preferable from the viewpoint of ease of controlling the material form, handleability and leukocyte-removing capability.

Nonwoven fabric is the most preferable from the viewpoint of ease of controlling performance characteristics.

The average pore size of the porous material is preferably less than 100 $\mu$m and not less than 1.0 $\mu$m. When the average pore size is less than 1.0 $\mu$m, the fluidity of blood is undesirably low, namely, the resistance to flow is undesirably increased. On the other hand, when the average pore size is 100 $\mu$m or more, the frequency of contact with leukocytes is undesirably decreased because of a decrease in the surface area, resulting in a decreased leukocyte removal rate. In view of the above, the average pore size of the porous material is more preferably less than 80 $\mu$m and not less than 3 $\mu$m, most preferably less than 60 $\mu$m and not less than 5 $\mu$m.

The term "average pore size" used herein means the diameter of pores determined by a mercury injection method. On the basis of values measured by the mercury injection method (Poresizer 9320, mfd. by Shimadzu Corp.), a graph is drawn by plotting pore volume on the axis of ordinate corresponding to individual pore sizes on the axis of abscissa, and the average pore size is defined as a value corresponding to the peak of the graph (a mode). As the values measured by the mercury injection method, values measured in a pressure range of 1 to 2650 psia are used.

In the present invention, when the form of the leukocyte-removing material is a nonwoven fabric form, the fiber diameter is preferably thin for increasing the frequency of contact with leukocytes. The average fiber diameter is preferably less than 100 $\mu$m and not less than 1 $\mu$m. From the viewpoint of leukocyte-removing properties, the average fiber diameter is more preferably less than 50 $\mu$m and not less than 1 $\mu$m, most preferably less than 30 $\mu$m and not less than 1 $\mu$m.

The average diameter of fibers constituting the nonwoven fabric is determined, for example, by taking scanning electron micrographs of the fibers constituting the nonwoven fabric, measuring the diameter of 100 or more of the fibers selected at random, and calculating the number average of the measured values.

In the leukocyte-removing material of the present invention, the basis weight of the nonwoven fabric can be measured by a well-known test method and is preferably as large as possible from the viewpoint of strength. Specifically, the basis weight is preferably 15 g/m$^2$ or more. On the other hand, when the basis weight is too large, the flowability of blood is deteriorated. Therefore, the upper limit of the basis weight is preferably less than 200 g/m$^2$. The basis weight of the nonwoven fabric is more preferably less than 150 g/m$^2$ and not less than 20 g/m$^2$, most preferably less than 100 g/m$^2$ and not less than 20 g/m$^2$.

As the nonwoven fabric used in the present invention, there may be used either a single nonwoven fabric or a material obtained by laminating two or more nonwoven fabrics different in basis weight or average fiber diameter.

The leukocyte-removing material of the present invention is especially excellent in biocompatibility and can suppress complement activation or bradykinin production. Therefore, the leukocyte-removing material of the present invention can be specified by its high biocompatibility.

The concentration of a complement activated by the contact of the leukocyte-removing material with blood is preferably low. The concentration of the activated complement is preferably less than 10 times and not less than 0.5 time as high as that before the contact. As an indication of the complement activation, there can be employed the concentration of an activated complement C3a or C4a, which is easily formed, and the biocompatibility can be satisfactorily evaluated by this indication. When the factor of hydrophilicity is less than 30%, a large amount of hydrophilic groups such as hydroxyl groups are present, so that the concentration of the activated complement is increased, namely, the biocompatibility is not high. Therefore, such a factor of hydrophilicity is not very desirable. Accordingly, the concentration of the activated complement is more preferably less than 8 times and not less than 0.5 time, most preferably less than 6 times and not less than 0.5 time, as high as that before the contact.

The concentration of the activated complement can be measured by a method such as a well-known radioimmunoassay with two antibodies [Nippon Rinsho (Japanese Clinic) Vol. 53, Special Number (the last volume) (1995)].

If there is no heating step, a peroxide produced by the irradiation of a polyolefin with a radiation acts as a negative charge, so that the bradykinin concentration is increased, namely, the biocompatibility is not high. Therefore, the absence of the heating step is not very desirable.

The concentration of bradykinin produced by the contact of the leukocyte-removing material of the present invention with blood is preferably low. The bradykinin concentration after the contact is preferably less than 100 times and not less than 1 time, more preferably less than 80 times and not less than 1 time, most preferably less than 60 times and not less than 1 time, as high as that before the contact.

The bradykinin concentration can easily be measured by a method such as a well-known radioimmuno-assay, enzyme immunoassay or the like.

The leukocyte-removing material of the present invention preferably has only a small amount of residual radicals after the irradiation with a radiation from the viewpoint of the stability of the material and the stability of the hydrophilicity. The amount of radicals in the polyolefin can be measured by means of an electron spin resonance (ESR) apparatus. The amount of residual radicals can be determined also by the following method: at the time of ESR measurement, manganese radicals are measured simultaneously with the measurement for the leukocyte-removing material, and there is used a radical intensity ratio obtained by dividing a maximum peak due to radicals remaining in the leukocyte-removing material by a peak due to manganese radicals.

The radical intensity ratio is preferably low because when radicals remain in the material, they deteriorate the material.

In addition, it was found that when the material is brought into contact with blood, the bradykinin concentration is increased by the contact if the radical intensity ratio is high.

The radical intensity ratio is preferably less than 1/g. When the radical intensity ratio is 1/g or more, the bradykinin concentration after the contact is undesirably 100 times or more as high as that before the contact. The radical intensity ratio is more preferably less than 0.5/g, most preferably less than 0.1/g.

The hydrophilicity of the leukocyte-removing material of the present invention is preferably invariant for a long period of time. Specifically, it is preferably stable for at least 6 months, more preferably 1 year or more, most preferably 3 years or more, under storage conditions for using the leukocyte-removing material as a medical supply.

The leukocyte-removing material of the present invention can be effectively used in a leukocyte-removing filter apparatus by packing it into a container having at least an inlet and an outlet.

When the leukocyte-removing material is used as a packing in the leukocyte-removing filter apparatus, the specification of the packing density is important because the state of pores varies depending on the packing density.

In the leukocyte-removing filter apparatus according to the present invention, the packing density is preferably less than 0.40 g/cm$^3$ and not less than 0.01 g/cm$^3$. When the packing density is less than 0.01 g/cm$^3$, the frequency of contact with leukocytes is undesirably decreased. On the other hand, when the packing density is 0.40 g/cm$^3$ or more, the pores are undesirably deformed or blocked, resulting in narrowed blood flow paths. In view of the above, the packing density is more preferably less than 0.35 g/cm$^3$ and not less than 0.01 g/cm$^3$, most preferably less than 0.30 g/cm$^3$ and not less than 0.05 g/cm$^3$.

When the leukocyte-removing material is used as a packing in the leukocyte-removing filter apparatus, a spacer material can be laminated between sheets of the leukocyte-removing material. When such a laminated structure is used, a pressure change is caused in a blood flow, resulting in aggregation and dispersion of hemocytes, and hence leukocytes can be efficiently removed.

When the leukocyte-removing material and the spacer material are laminated, they are satisfactorily laminated in a direction perpendicular to a blood flow and/or in a cylindrical form. In this case, the specification of the ratio of the leukocyte-removing material to the spacer material (hereinafter referred to as the lamination ratio) is important. The lamination ratio is calculated by the following equation.

Lamination ratio=thickness of leukocyte-removing material/thickness of spacer material When the lamination ratio is less than 10 and not less than 0.5, an efficient pressure change is caused, so that satisfactory removal of leukocytes is possible. When the lamination ratio is less than 0.5, the amount of the leukocyte-removing material is relatively decreased, so that the size of the leukocyte-removing filter apparatus should be increased. On the other hand, when the lamination ratio is 10 or more, the thickness of the leukocyte-removing material is too large, no sufficient pressure change can be caused in a blood flow. In view of the above, the lamination ratio is more preferably less than 8 and not less than 0.5, most preferably less than 5 and not less than 0.5.

The spacer layer referred to herein is a layer in which blood flows more easily than in the leukocyte-removing material layers. As the spacer layer, there is used, for example, a wide-meshed net of metal or synthetic resin, inorganic fiber, synthetic fiber, or nonwoven fabric having an average fiber diameter larger than that of the nonwoven fabric used as the leukocyte-removing filter layers.

As the spacer material used in the leukocyte-removing filter apparatus according to the present invention, a reticular and/or woven-fabric-like material or a nonwoven-fabric-like material is satisfactorily used. The mesh size of such a spacer is preferably less than 1,000-mesh and not less than 3-mesh. When the mesh size is 1,000-mesh or more, the spacer material undesirably have too fine meshes, so that no sufficient pressure change can be caused in the flow even if the spacer material is laminated with the leukocyte-removing material. On the other hand, when the mesh size is less than 3-mesh, the leukocyte-removing material undesirably enters the meshes of the mesh material, so that no sufficient pressure change can be caused in the flow.

As a method for sterilizing the leukocyte-removing material of the present invention, well-known methods such as radiation sterilization, wet heat sterilization, chemical sterilization, etc. are used.

The leukocyte-removing material can be sterilized preferably by wet heat sterilization.

The leukocyte-removing material of the present invention is preferably sterilized in a wet state together with a filling liquid from the viewpoint of its handleability at the time of use and its stability during the sterilization. As the filling liquid, any liquid may be satisfactorily used so long as it does not deteriorate the leukocyte-removing material. The filling liquid is preferably an aqueous solution which has no undesirable influence on blood and the like even if the filling liquid remains at the time of use of the leukocyte-removing material. Particularly when leukocytes are removed from a blood component, waters such as distilled water for injection, ion-exchanged water, ultrafiltered water, etc., and aqueous solutions containing salts are preferably used.

The process for producing a hydrophilized polyolefin of the present invention is explained below. By carrying out a step of irradiating a polyolefin with a radiation in a dose of less than 300 kGy and not less than 15 kGy, and then a step of heating said material irradiated with the radiation, at a temperature of lower than 125° C. and not lower than 75° C., the polyolefin can be hydrophilized and can be allowed to retain hydrophilicity for a long period of time.

The irradiation of the raw material with a radiation in the presence of oxygen is preferable because it permits efficient hydrophilization. For satisfactory hydrophilization of the polyolefin, the oxygen concentration is preferably less than 100% and not less than 0.1%, more preferably less than 50% and not less than 0.1%. Therefore, the polyolefin can be efficiently hydrophilized by its irradiation in air.

In addition, the specification of the irradiation dose of the radiation is also important in suppressing the deterioration of the raw material. An irradiation dose of the radiation required for hydrophilizing the raw material is less than 300 kGy and not less than 15 kGy. When the irradiation dose of the radiation is less than 15 kGy, no sufficient hydrophilicity is undesirably attainable even if the heating step is carried out in addition to the irradiation. On the other hand, when the irradiation dose of the radiation is 300 kGy or more, the deterioration of the raw material is undesirably remarkable. The irradiation dose of the radiation is more preferably less than 200 kGy and not less than 15 kGy, most preferably less than 100 kGy and not less than 30 kGy.

As the radiation, electron beams, δ-rays, α-rays, β-rays, X-rays, etc. are used. Electron beams or γ-rays are preferably used form the viewpoint of the efficiency of hydrophilization. Electron beams are most preferably used from the viewpoint of the suitable transmittance of the radiation.

For the heat treatment after the irradiation, any method may be used so long as it is intended for heating. As a preferable heating method, heating at a dry state, heating in hot water, or heating in high-pressure steam is effectively employed. The heating in hot water is most preferably employed from the viewpoint of ease of operation.

The heating temperature is preferably lower than 125° C. and not lower than 75° C. because in this temperature range, the peroxide produced is cleaved and the amount of residual radicals can be rapidly reduced. When heating temperature is lower than 75° C., the cleavage of the peroxide is undesirably not sufficient. In this case, when the resulting material is used as a leukocyte-removing material, the hemocompatibility is deteriorated by the residual peroxide, so that bradykinin production and the like are caused. Therefore, such a heating temperature is not desirable also from the viewpoint of biocompatibility. When the heating temperature is 125° C. or higher, the cleavage of the peroxide is sufficient but the deterioration of the raw material is undesirably accelerated. The heating temperature should be lower than the melting point of the raw material. In view of the above, the heating temperature is more preferably lower than 125° C. and not lower than 80° C., most preferably lower than 121° C. and not lower than 80° C.

In addition, the specification of the heating time is also important. The heating time is preferably less than 200 minutes and not less than 1 minute from the viewpoint of the cleavage of the peroxide and the reduction of the amount of residual radicals. When heating time is less than 1 minute, the cleavage of the peroxide is undesirably not sufficient. When the heating is conducted for 200 minutes or more, the amount of residual radicals becomes very slight in 200 minutes. Therefore, such heating is not efficient. Thus, the heating time is more preferably less than 120 minutes and not less than 10 minutes, most preferably less than 120 minutes and not less than 15 minutes. When such a heating time is employed, the cleavage of the peroxide and the reduction of the amount of residual radicals can be efficiently achieved.

According to the process of the present invention, hydrophilicity can be efficiently imparted to a polyolefin. Since the resulting hydrophilic polyolefin is not changed in hydrophilicity over a long period of time, is hardly deteriorated as material and contains only a small amount of residual radicals and the like, it is suitably used for various purposes, in particular, medical purposes and the like.

The present invention is illustrated in further detail with reference to the following examples.

EXAMPLE 1

Polypropylene nonwoven fabrics (average fiber diameter: 1.7 μm, basis weight: 60 g/m2, polypropylene content 99.99%) were irradiated with electron beams in five irradiation doses (A: 15 kGy, B: 50 kGy, C: 70 kGy, D: 100 kGy, and E: 150 kGy), respectively, in air. Each irradiated nonwoven fabric was poured into hot water at 98° C. to be heat-treated for 60 minutes. After the heat treatment, the nonwoven fabric was taken out of the hot water and dried in vacuo at 40° C. for 40 hours to obtain a desired leukocyte-removing material. Table 1 shows the factor of hydrophilicity of the leukocyte-removing materials after the hydrophilization. A part of each leukocyte-removing material was compressed and its infrared absorption spectrum was measured with a Fourier transform infrared absorption spectrophotometer (FT/IR-7300, mfd. by Nippon Bunko Co., Ltd.) to confirm an absorption due to hydroxyl group near 3,700 cm$^{-1}$ and an absorption due to a keto group near 1,700 cm$^{-1}$.

For evaluating the leukocyte-removing capability of each leukocyte-removing material, five discs with a diameter of 0.68 cm were cut out of each leukocyte-removing material and were packed as filters (packing density 0.1 g/cm3) into a container with a capacity of 1 ml having an inlet and an outlet. When priming was conducted by placing distilled water for injection in the container as a packing liquid, the priming could be easily achieved. Thus, a desired leukocyte-removing column could be produced.

Into the obtained column was introduced 3 ml of human fresh blood containing ACD-A (blood : ACD-A=8:1 by volume) at a flow rate of 0.5 ml/min through the inlet of the column by the use of a syringe pump, and the treated blood was recovered through the outlet of the column.

The leukocyte removal rate was calculated by counting leukocytes before and after the treatment by Turk staining to determine the leukocyte concentrations before and after the treatment. The leukocyte concentration before the treatment was 5,200 cells/μL. The leukocyte removal rate is shown in Table 1.

The leukocyte removal rate (%) was calculated by the following equation:

Leukocyte removal rate=100×(leukocyte concentration before treatment−leukocyte concentration after treatment)/leukocyte concentration before treatment In this case, platelets were measured with a well-known blood counter. The platelet concentration before the treatment was 400,000 cells/μL. The platelet removal rate is shown in Table 1.

The platelet removal rate (%) was calculated by the following equation:

Platelet removal rate=100×(platelet concentration before treatment−platelet concentration after treatment)/platelet concentration before treatment The pressure before the column was measured with a manometer. The results are shown in Table 1.

Further, in this case, the concentration of an activated complement (C3a) (SRL Corp.) and the concentration of bradykinin (SRL Corp.) were measured. The C3a concentration was 100 ng/ml before the treatment, and the bradykinin concentration was 100 pg/ml before the treatment.

The degree of activation for C3a and the degree of bradykinin production were calculated by dividing the concentration of each of these substances after the treatment by the concentration thereof before the treatment. They are shown in Table 1.

In addition, the radical intensity of each nonwoven fabric was measured with an electron spin resonance apparatus (JES-FE2XG, mfd. by Nippon Denshi Co., Ltd.). In this case, as a control, there were used manganese radicals (an ESR marker sample manufactured by Nippon Denshi Co., Ltd. was used: the distance between the third and fourth signals among 6 ESR spectra of manganese ion (Mn2+) contained in MnO is constant (86.9 Gauss) irrespective of frequency, and the fourth peak is used as a reference peak). The radical instensity ratio obtained relative to manganese is shown in Table 1.

Further, the leukocyte-removing material obtained by employing the irradiation dose D was stored at room temperature in the presence of air for each of 30 days and 90 days. In both cases, the factor of hydrophilicity of the leukocyte-removing material after the storage was 35%.

Still further, the leukocyte-removing material obtained by employing the irradiation dose D was subjected to an accelerated storage test under the following conditions. The conditions of the accelerated storage test were 60° C. for 6 weeks. (Such conditions correspond to storage for 3 years; see GUIDELINES FOR INDUSTRIAL RADIATION STERILIZATION OF DISPOSABLE MEDICAL PRODUCTS (IAEA-TECDOC-539) 4.2.1 Materials compatibility). The factor of hydrophilicity of the leukocyte-removing material after the storage was 35% as before the storage.

In addition, the leukocyte-removing material obtained by employing the irradiation dose D was sterilized in water at 121° C. for 20 minutes by autoclaving. The sterilized leukocyte-removing material was dried at 40° C. for 20 hours. The factor of hydrophilicity of the thus treated leukocyte-removing material was 35%, namely, the hydrophilicity was not deteriorated by the sterilization.

COMPARATIVE EXAMPLE 1

The process of Example 1 was repeated except for omitting the irradiation with electron beams. In this case, the factor of hydrophilicity of the same nonwoven fabric as in Example 1 was 41%. A column packed with the nonwoven fabric was produced in the same manner as in Example 1 and subjected to priming with distilled water for injection, but the priming could not be conducted because the pressure of the priming liquid on the inlet side was increased. Therefore, the nonwoven fabric was hydrophilized with 1 ml of ethanol and then primed with 5 ml of distilled water for injection.

In the same blood test as in Example 1, the number of leukocytes was decreased to 1,300 cells/$\mu$L from 5,200 cells/$\mu$L, the number of leukocytes before the treatment, namely, the leukocyte removal rate was 75%. In this case, the number of platelets was decreased to 80,000 cells/$\mu$L from 400,000 cells/$\mu$L, the number of platelets before the treatment, namely, the platelet removal rate was 80%. Thus, the leukocyte removal rate was decreased by a one-sided flow of leukocytes which was attributable to low wettability. During the blood flowing, the pressure before the column of 100 mmHg was increased owing in all probability to the low wettability. In addition, the activated complement (C3a) concentration ratio and the bradykinin concentration ratio were determined in the same manner as in Example 1 and found to be 1.2 and 1.1, respectively.

EXAMPLE 2

A polyethylene foamed sheet (bore diameter 50 $\mu$m, thickness 10 mm) was irradiated with electron beams in an irradiation dose of 100 kGy in air by means of an electron beams irradiation apparatus. The irradiated foamed sheet was poured into hot water at 98° C. to be heat-treated for 60 minutes. After the heat-treatment, the foamed sheet was taken out of the hot water and dried in vacuo at 40° C. for 40 hours to obtain a desired leukocyte-removing material. The factor of hydrophilicity of the leukocyte-removing material after the hydrophilization was 37%. A part of this leukocyte-removing material was compressed and its infrared absorption spectrum was measured with a Fourier transform infrared absorption spectrophotometer (FT/IR-7300, mfd. by Nippon Bunko Co., Ltd.) to confirm an absorption due to hydroxyl group near 3,700 cm$^{-1}$ and an absorption due to a keto group near 1,700 cm$^{-1}$.

For evaluating the leukocyte-removing capability of the leukocyte-removing material, two discs with a diameter of 0.68 cm were cut out of the leukocyte-removing material and were packed as filters (packing density 0.05 g/cm$^3$) into a container with a capacity of 1 ml having an inlet and an outlet. When priming was conducted by placing distilled water for injection in the container as a packing liquid, the priming could easily be achieved. Thus, a desired leukocyte-removing column could be produced.

Into the obtained column was introduced 5 ml of human fresh blood containing ACD-A (blood: ACD-A=8:1 by volume) at a flow rate of 0.5 ml/min through the inlet of the column by the use of a syringe pump, and the treated blood was recovered through the outlet of the column.

The leukocyte removal rate was calculated by counting leukocytes before and after the treatment by Turk staining to determine the leukocyte concentrations before and after the treatment. The leukocyte concentration before the treatment was 5,200 cells/$\mu$L, and that after the treatment 800 cells/$\mu$L. Thus, the leukocyte removal rate was 84.6%. In this case, platelets were measured with a well-known blood counter to find that the platelet concentration before the treatment was 400,000 cells/$\mu$L and that after the treatment 390,000 cells/$\mu$L. The platelet removal rate was calculated in the same manner and found to be 2.5%. The pressure before the column was 10 mmHg and was not increased. In addition, the activated complement (C3a) concentration ratio and the bradykinin concentration ratio were determined in the same manner as in Example 1 and found to be 2.1 and 3.1, respectively.

COMPARATIVE EXAMPLE 2

The same evaluation as in Example 2 was carried out except for omitting the irradiation with electron beams. In this case, the factor of hydrophilicity of the same foamed sheet as in Example 2 was 43%. Consequently, blood hardly flowed because of the insufficient hydrophilicity and blood flowing was difficult because of a pressure increase.

EXAMPLE 3

The process of Example 1 was repeated except for changing the irradiation dose of electron beams to 70 kGy, to obtain a leukocyte-removing material of the present invention. The factor of hydrophilicity of this leukocyte-removing material was 36%. The nonwoven fabric as the leukocyte-removing material was cut into two 15 cm×70 cm sheets, which were laminated with a sheet obtained by cutting a spacer material (a polypropylene mesh (mesh size: 10-mesh)) to the same dimensions as above. The resulting laminate was rolled up into a cylinder by the use of a core with a diameter of 1 cm. Thus, the cylinder having a diameter of 4.2 cm and a length of 15 cm (lamination ratio: 1) was obtained. In the upper part and lower part of the cylinder, the edges of the laminate were stuck together with a polyurethane adhesive, and a nozzle having a through-hole was attached to the center of one side of the cylinder. The cylinder was packed into a container equipped with a nozzle on one side, to produce a desired leukocyte-removing filter apparatus (packing density: 0.02 g/cm$^2$). The apparatus was filled with distilled water for injection and sterilized at 121° C. for 20 minutes by autoclaving. In this case, the inlet of column was on the nozzle non-attachment side and the outlet of column was on the nozzle attachment side.

Into the thus obtained column was introduced 3,000 ml of bovine fresh blood containing ACD-A (blood:ACD-A=8:1 by volume) at a flow rate of 50 ml/min through the inlet of the column by the use of a roller pump, and the treated blood was recovered through the outlet of the column.

The leukocyte removal rate was calculated by counting leukocytes before and after the treatment by Turk staining to determine the leukocyte concentrations before and after the treatment. The leukocyte concentration before the treatment was 5,000 cells/µL, and that after the treatment 30 cells/µL. Thus, the leukocyte removal rate was 99.4%. The platelet concentration was 450,000 cells/µL before the treatment and 360,000 cells/µL after the treatment, namely, the platelet removal rate was 20%. The pressure before the column was 25 mmHg and was not increased.

EXAMPLE 4

The process of Example 1 was repeated except for changing the irradiation dose of electron beams to 100 kGy, to obtain a leukocyte-removing material of the present invention. This leukocyte-removing material had a factor of hydrophilicity of 35% and a CWST value of 39 dyne/cm. The leukocyte-removing material was cut into a sheet 12.5 cm square. This sheet of nonwoven fabric and the same spacer material as in Example 3 were laminated in a lamination ratio of 2 so as to be packed into a container having an inlet and an outlet, whereby a desired leukocyte-removing filter apparatus (packing density: 0.25 g/cm$^2$) was obtained.

Into the thus obtained column was introduced 1,000 ml of bovine fresh blood containing ACD-A (blood:ACD-A=8:1 by volume) at a flow rate of 25 ml/min through the inlet of the column by the use of a roller pump, and the treated blood was recovered through the outlet of the column.

The leukocyte removal rate was calculated by counting leukocytes before and after the treatment by Turk staining to determine the leukocyte concentrations before and after the treatment. The leukocyte concentration before the treatment was 5,700 cells/µL, and that after the treatment 41 cells/µL. Thus, the leukocyte removal rate was 99.2%. In this case, the platelet concentration was 350,000 cells/µL before the treatment and 280,000 cells/µL after the treatment, namely, the platelet removal rate was 20%. The pressure before the column was 25 mmHg and was not increased.

EXAMPLE 5

A polypropylene nonwoven fabric (average fiber diameter: 2.9 µm, basis weight: 90 g/m$^2$, polypropylene content 99.99%) was irradiated with electron beams in an irradiation dose of 70 kGy in air. The factor of hydrophilicity of the irradiated nonwoven fabric was 36%. The irradiated nonwoven fabric was stored under the same conditions as in Example 1 to find that after 30 days of storage, 90 days of storage and accelerated storage, the factor of hydrophilicity of the irradiated nonwoven fabric was 35%, 34% and 29%, respectively.

COMPARATIVE EXAMPLE 3

A polypropylene nonwoven fabric (average fiber diameter: 1.7 µm, basis weight: 60 g/m$^2$, polypropylene content 99.99%) was irradiated with electron beams in an irradiation dose of 500 kGy in air. The irradiated nonwoven fabric was exposed to hot air at 98° C. to be heat-treated for 60 minutes. The factor of hydrophilicity of the leukocyte-removing material after the hydrophilization was 28%. The leukocyte removal rate, platelet recovery, column pressure loss, activated complement (C3a) concentration ratio, and bradykinin concentration ratio were determined by the same methods as in Example 1 and found to be 99.6%, 20%, 25 mmHg, 20 and 150, respectively. Thus, it was found that the biocompatibility had been deteriorated. In addition, it was found that by the excessive irradiation, the tensile strength at break had been decreased to a quarter of that before the irradiation.

COMPARATIVE EXAMPLE 4

A polypropylene nonwoven fabric (average fiber diameter: 1.7 µm, basis weight: 60 g/m$^2$, polypropylene content 99.99%) was irradiated with plasma for 120 seconds in a hydrogen stream by means of a plasma irradiation apparatus. After the irradiation, the factor of hydrophilicity of the nonwoven fabric was 0%. Then, the irradiated nonwoven fabric was stored at 60° C. for 6 weeks in the same manner as in Example 1 to find that its factor of hydrophilicity was decreased to 41%. Thus, no lasting hydrophilicity could be imparted.

COMPARATIVE EXAMPLE 5

A polypropylene nonwoven fabric (average fiber diameter: 1.7 µm, basis weight: 60 g/m$^2$, polypropylene content 99.99%) was immersed in a 20 w/w % ethanolic solution of an ethylene-vinyl alcohol copolymer (vinyl alcohol content 20%) for 10 minutes to be coated with the solution. The nonwoven fabric was taken out of the solution and dried at 50 for 10 hours to obtain coated nonwoven fabric. When this nonwoven fabric was sterilized in water (water: the nonwoven fabric=100:1 by weight) at 121° C. for 20 minutes by autoclaving, appearance of white turbidity was caused by the peeling-off of the ethylene-vinyl alcohol copolymer coating.

TABLE 1

|   | Factor of hydro- philicity | Leukocyte removal rate (%) | Platelet removal rate (%) | Pressure loss (mmHg) | C3a concentra- tion ratio | Bradykinin concentra- tion ratio | Radical intensity ratio | Priming properties |
|---|---|---|---|---|---|---|---|---|
| A | 39 | 90.2 | 25 | 35 | 1.5 | 1.2 | 0.01 | Good |
| B | 37 | 99.0 | 20 | 25 | 1.6 | 1.4 | 0.01 | Good |
| C | 36 | 99.5 | 15 | 18 | 2.0 | 1.5 | 0.01 | Good |
| D | 35 | 99.6 | 10 | 15 | 2.1 | 1.5 | 0.01 | Good |
| E | 33 | 99.6 | 15 | 12 | 3.5 | 5.1 | 0.01 | Good |

INDUSTRIAL APPLICABILITY

Since the leukocyte-removing material of the present invention is composed substantially of a polyolefin, it is so excellent in thermal stability that its structure is not changed even by wet heat sterilization. Moreover, since said leukocyte-removing material is a suitably hydrophilized material, it is excellent in wettability, can easily be primed, and has a high leukocyte-removing capability. The hydrophilicity of said leukocyte-removing material is not deteriorated over a long period of time, and hence the leukocyte-removing material sufficiently retains its excellent hydrophilicity until it is used as a medical supply.

In addition, a suitable hydrophilicity can be imparted to a hydrophobic polyolefin material by practicing the process for producing a hydrophilized polyolefin of the present invention. Furthermore, the hydrophilicity is retained for a long period of time without being deteriorated over a long period of time. Therefore, the polyolefin material produced according to the production process of the present invention is suitable as a material for medical supplies such as, in particular, a leukocyte-removing material which requires wet heat sterilization.

What is claimed is:

1. A porous leukocyte-removing material composed substantially of a polyolefin, the factor of hydrophilicity of the surface of said leukocyte-removing material being less than 40% and not less than 30%, wherein the average pore size of said porous material is less than 100 μm and not less than 1.0 μm, wherein said porous material is a structure made of a non-woven fabric, and which has groups selected from the class consisting of hydroxyl groups and keto groups on the surface, said non-woven fabric weighing at least 15 g/m² but less than 200 g/m².

2. A leukocyte-removing material according to claim 1, wherein said factor of hydrophilicity is less than 39% and not less than 32%.

3. A leukocyte-removing material according to claim 1, wherein the average pore size of said porous material is less than 100 μm and not less than 1.0 μm.

4. A leukocyte-removing material according to claim 1, wherein the average fiber diameter of said nonwoven fabric is less than 100 μm and not less than 1 μm.

5. A leukocyte-removing material according to claim 1, wherein the polyolefin includes at least polypropylenes.

6. A leukocyte-removing material according to claim 1, which is excellent in biocompatibility.

7. A leukocyte-removing material according to claim 1, which is not changed in hydrophilicity over a long period of time.

8. A hydrophilized leukocyte-removing material composed substantially of a polyolefin, characterized by having an excellent biocompatibility and being not changed in hydrophilicity over a long period of time.

9. A leukocyte-removing material according to claim 8, obtainable by a production process comprising a step of irradiating a material composed substantially of a polyolefin with a radiation in a dose of less than 300 kGy and not less than 15 kGy, and a step of heating said material at a temperature of lower than 125° C. and not lower than 75° C. after the irradiation with the radiation.

10. A leukocyte-removing material according to claim 1, obtainable by a production process comprising a step of irradiating a material composed substantially of a polyolefin with a radiation in a dose of less than 300 kGy and not less than 15 kGy, and a step of heating said material at a temperature of lower than 125° C. and not lower than 75° C. after the irradiation with the radiation.

11. A process for producing a hydrophilized polyolefin which comprises a step of irradiating a polyolefin with a radiation in a dose of less than 300 kGy and not less than 15 kGy, and a step of heating said polyolefin at a temperature of lower than 125° C. and not lower than 75° C. after the irradiation with the radiation.

12. A process according to claim 11, wherein said radiation is electron beams.

13. A process according to claim 11, wherein said heating step is treatment with hot water.

14. A process according to claim 11, wherein the hydrophilized polyolefin is a biocompatible material.

15. A process according to claim 11, wherein at least one of said radiation irradiation step and said heating step performs sterilization.

16. A method for removing leukocytes from a leukocyte-containing fluid which comprises bringing the leukocyte-containing fluid into contact with a leukocyte-removing material composed substantially of a polyolefin and having a factor of hydrophilicity of the surface of less than 40% and not less than 30%, produced by the process of claim 11, and recovering the fluid filtered through the leukocyte-removing material.

17. A hydrophilized polyolefin produced by the method of claim 11 and having a factor of hydrophilicity of the surface of less than 40% and not less than 30%.

18. A hydrophilized polyolefin according to claim 17, wherein said factor of hydrophilicity is less than 39% and not less than 32%.

19. A hydrophilized polyolefin according to claim 17, which is porous material.

20. A hydrophilized polyolefin according to claim 19, wherein the average pore size of said porous material is less than 100 μm and not less than 1.0 μm.

21. A hydrophilized polyolefin according to claim 19, wherein said porous material is a structure made of fiber.

22. A hydrophilized polyolefin according to claim 21, wherein said structure made of fiber is a non-woven fabric.

23. A hydrophilized polyolefin according to claim 22, wherein the average fiber diameter of said non-woven fiber fabric is less than 100 μm and not less than 1 μm.

24. A hydrophilized polyolefin according to claim 17, which has groups selected from the class consisting of hydroxyl groups and keto groups on the surface.

25. A hydrophilized polyolefin according to claim 17, wherein the polyolefin includes at least polypropylenes.

26. A leukocyte-removing material according to claim 1, wherein concentration of a complement C3a OR C4a activated by contact of the leukocyte-removing material with blood is less than 10 times and not less than 0.5 times as high as that before the contact.

27. A leukocyte-removing material according to claim 1, wherein concentration of bradykinin produced by contact of the leukocyte-removing material with blood is less than 100 times and not less than 1 time as high as that before the contact.

28. A leukocyte-removing filter apparatus which comprises a container having at least an inlet and an outlet and a leukocyte-removing material comprising a hydrophilized polyolefin of claim 17, packed into said container.

29. The leukcyte-removing filter apparatus of claim 28, wherein a packing density of said leukocyte-removing material is less than 0.40 g/cm³ and not less than 0.01 g/cm³.

30. The leukocyte-removing filter apparatus of claim 28, wherein a spacer material is laminated between sheets of said leukocyte-removing material and both said materials are in a cylindrical form.

31. The leukocyte-removing filter apparatus of claim 30, wherein a lamination ratio of said leukocyte-removing filter and said spacer material is less than 10 and not less than 0.5.

* * * * *